United States Patent
Quellet et al.

(10) Patent No.: US 7,205,340 B2
(45) Date of Patent: Apr. 17, 2007

(54) POLYMERIC NANOPARTICLES INCLUDING OLFACTIVE COMPONENTS

(76) Inventors: Christian Quellet, Rue Neuve 20, CH-2502 Biel (CH); Jutta Hotz, Gemsenstrasse 3, Zurich CH-8006 (CH); Marc Balmer, Im Aegelsee 5, Unterengstringen CH-8006 (CH)

( * ) Notice: Subject to any disclaimer, the term of this patent is extended or adjusted under 35 U.S.C. 154(b) by 367 days.

(21) Appl. No.: 10/240,978

(22) PCT Filed: Apr. 6, 2001

(86) PCT No.: PCT/EP01/03986
§ 371 (c)(1),
(2), (4) Date: Mar. 5, 2003

(87) PCT Pub. No.: WO01/79303
PCT Pub. Date: Oct. 25, 2001

(65) Prior Publication Data
US 2003/0181540 A1 Sep. 25, 2003

(30) Foreign Application Priority Data
Apr. 15, 2000 (EP) .................................. 00108313

(51) Int. Cl.
*A61L 2/00* (2006.01)
(52) U.S. Cl. .................... 523/102; 510/349; 512/4; 424/401; 428/402.2
(58) Field of Classification Search ................ 523/102; 510/349; 512/4; 424/401; 428/402.2
See application file for complete search history.

(56) References Cited

U.S. PATENT DOCUMENTS

| | | | | |
|---|---|---|---|---|
| 5,155,193 A | * | 10/1992 | Georges et al. | 526/230.5 |
| 5,506,201 A | * | 4/1996 | McDermott et al. | 512/4 |
| 5,972,508 A | * | 10/1999 | Boeckh et al. | 428/402.2 |
| 6,126,953 A | * | 10/2000 | Costa et al. | 424/401 |
| 6,147,046 A | * | 11/2000 | Shefer et al. | 510/349 |
| 6,150,310 A | * | 11/2000 | Sivik et al. | 510/107 |
| 6,184,188 B1 | * | 2/2001 | Severns et al. | 510/101 |
| 6,518,334 B1 | * | 2/2003 | Calhoun et al. | 524/47 |

FOREIGN PATENT DOCUMENTS

| | | |
|---|---|---|
| DE | 967860 | 12/1957 |
| DE | 0839902 A2 | 10/1997 |
| EP | 0346034 A2 | 12/1989 |
| EP | 617051 A2 * | 9/1994 |
| EP | 0617051 A2 | 9/1994 |
| EP | 0925776 A2 | 6/1999 |
| JP | 63-122796 | 5/1988 |
| WO | WO 98/28396 | 7/1998 |

OTHER PUBLICATIONS

International Search Report from PCT/EP01/03986 filed Apr. 6, 2001.

* cited by examiner

Primary Examiner—David W. Wu
Assistant Examiner—Henry S. Hu
(74) Attorney, Agent, or Firm—Norris McLaughlin & Marcus PA

(57) ABSTRACT

The polymeric nanoparticles including olfactive components have a glass temperature of >50° C. They are obtainable by continuously adding a monomer component and an olfactive component to an aqueous solution. The aqueous solution comprises a first initiator and an emulsifier. The added components are distributed in the aqueous solution to obtain reaction mixture while the polymerization of the monomer component is started at the first temperature. The liquid monomer component and the olfactive component are added continuously while a second initiator is added dropwise to the reaction mixture and the first temperature is maintained. After terminating the addition of liquid monomer component and the olfactive component the temperature of the reaction mixture is increased to a second temperature and a third initiator is added dropwise.

15 Claims, No Drawings

POLYMERIC NANOPARTICLES INCLUDING OLFACTIVE COMPONENTS

The present invention relates to polymeric nanoparticles including olfactive components which are useful as delivery system for olfactive components.

Olfactive component in the present context means fragrances, odour masking agents and mixtures thereof such as perfume compositions as well as precursors for the above.

A principal strategy currently employed in imparting odours to consumer products is the admixing of the fragrance directly into the product. There are, however, several drawbacks to this strategy. The fragrance material can be too volatile, resulting in fragrance loss during manufacturing, storage and use. Many fragrance materials are also unstable over time. This again results in loss of perfume during storage.

In many consumer products it is desirable for the fragrance to be released slowly over time. Since the most volatile fragrances, or "top notes" are responsible for the "fresh feeling" consumers experience, it is desirable that in addition to the less volatile fragrances of a fragrance composition also the more volatile fragrances are slowly released. Such slow release is commonly referred to as sustained release and is characterized, ideally, by a zero-order diffusion kinetics. For olfactive compositions, the signature of a zero-order diffusion kinetics is a constant value of the fragrance concentration in the gas phase in the vicinity of the substrate over a long period of time. In the language of perfumery, the gas phase around any substrate is called "headspace" and, accordingly, the fragrance concentration in this phase is called "headspace concentration". The headspace concentration is usually expressed in ng/l headspace.

To be perceived by the consumer, the fragrance headspace concentration must be higher than the so-called olfactive threshold, being the concentration below which the human nose perceives. Hence, long lasting means that the headspace concentration is maintained above the threshold concentration over a long period of time.

The olfactory performance of fragrances can alternatively be expressed in terms of "odour value". The odour value is the ratio of the actual headspace concentration (vapour pressure) of the fragrance to its olfactory threshold value, both expressed in ng/l.

Fragrances considered as top notes and those having odour values between 10,000 and 10,000,000 are preferred in the present invention.

Direct admixing of a fragrant composition in a product does generally not provide the desired zero-order release kinetics quoted above. Instead, a first order release kinetics is observed, which is marked by an exponential decrease of the headspace concentration. The kinetics of this first-order diffusion depends on the vapour pressure of the fragrance. Due to this vapour pressure dependence, top notes are perceived only over a very short period.

Therefore, it is highly desirable to provide a system that (i) protects the volatile top notes in a composition, (ii) improves the substantivity of these top notes on various substrates and (iii) imparts a long-lasting release of these top notes from various substrates over a long period of time, i.e. at least 24 hours, preferably at least 72 hours and more preferably at least 5 days.

A large amount of work has been devoted to the realization of fragrance delivery systems that expand the spectrum of fragrance perceived on substrates and improve the sustained release of fragrances.

Micro-encapsulation and inclusion complexes with cyclodextrines have been used to decrease volatility, improve stability and provide slow-release properties. However, cyclodextrines poured into water release the fragrance immediately, which limits their uses as controlled release systems in e.g. laundry care.

Spray drying, coacervation and interfacial polymerization are examples of technologies which are also used for encapsulating fragrances in detergents and laundry care products. Whereas these techniques may increase the amount of fragrances available in the washing liquor, they do not improve the sustained release of fragrance from substrates per se.

An important part of the fragrance composition initially added to detergent products, soaps and conditioners is lost by evaporation and dissolution in the wash and rinse water. Accordingly, an important amount of work has been devoted to the general problem of perfuming various substrates during washing and thereafter during the conditioning procedure in order to enhance fragrance deposition on the substrates and to provide a sustained release of fragrance during and after the drying stage.

A classical method for enhancing fragrance deposition is admixing the fragrance with surfactants and especially with cationic surfactants contained in conditioner compositions. An alternative route involves the preparation of solid particles by admixing the fragrance with amphiphilic polymers. EP-A 0 469 228 discloses a perfume carrier and delivery system which is claimed to be suitable for use in a wash liquor and which consists of a perfume, a hydrophobic solid, a branched or linear alcohol or ester and an amphiphilic polymer derived from monomers such as ethylene oxide, acrylic acid, styrenesulfonate, acrylamide and block copolymers thereof with polyoxypropylene or polyamide.

EP-A 0 346 034 discloses a process for preparing particles of wax encapsulated actives (like perfume) for use in cleaning products by (i) dispersing actives in molten wax, (ii) emulsifying the active/wax dispersion in aqueous surfactant solution, (iii) quenching the capsules by cooling and (iv) retrieving solidified capsules.

U.S. Pat. No. 5,506,201 discloses a method for producing a fragrance-containing solid particle of improved substantivity for incorporation into laundry detergents which comprises of a fat component and a solid surface active agent like sorbitan ester.

The methods of the above documents may improve the deposition of fragrance onto substrates when added to laundry care products. However, it is known that waxes and fats exude hydrophobic volatile molecules and therefore they do not significantly reduce the evaporation rate of the fragrances from the substrate during drying. Thus, these systems do generally not produce the desired sustained and controlled release action.

EP-A 0 617 051 discloses polymeric composition obtained by emulsion polymerization of unsaturated monomers in the presence of a fragrance. No details concerning the method to produce this polymer composition is disclosed.

JP-A 63/122796 discloses the use of a non fragrant latex in liquid products, such as laundry care products, comprising fragrances, to improve deposition and controlled release of fragrances on substrates. The polymer used is soft polyacrylate having low glass temperature bearing cationic or pseudo-cationic groups, and consisting essentially of poly-butylacrylate.

WO 98/28396 discloses a latex having particle sizes larger than 1 to 10 microns which are produced by suspension polymerization of vinyl monomers. A fragrance is incorporated by mixing it with the monomers prior to polymerization or by post-adding of the fragrance to the latex. The latex microparticles are surrounded by a polyhydroxy hydrocolloid layer which is claimed to enhance deposition of the perfume on substrates.

All the known systems may potentially improve perfume deposition on substrates but do not impart sustained, controlled release of volatile top notes to the substrates.

EP-A 0 925 776 discloses a polymer molecularly imprinted, with an organoleptic substance and prepared by solution or dispersion polymerisation in organic media, in the presence of the imprinting substance. The polymer used binds preferentially the olfactive components which have been used for imprinting. Examples of selective malodour recognition are given and some of the results with laundry care products suggest a better deposition and enhanced longevity of imprinting agents. There are, however, a number of drawbacks. First, solution polymerization is difficult to conduct at industrial scales. Second, subsequent grinding and sieving to obtain usable particles is required. Third, the use of an organic solvent is detrimentous to the final loading of the polymer, due to partition of the olfactive component between polymer and solvent.

One object of the present invention is, therefore, to provide a novel polymeric system for delivery of olfactive components or components and precursors thereof. In the following the term olfactive components or components also encompasses masking agents and precursors for olfactive components and masking agents.

A further object of the present invention is to provide polymeric nanoparticles for the delivery and uptake of olfactive components.

A further object of the present invention is to provide polymeric nanoparticles with enhanced substantivity to substrates and controlled sustained release for the olfactive components.

A special object of the present invention is to provide a new delivery system for top notes.

A further object of the present invention is to provide a new delivery system for olfactive components with sustained release at room temperature and with fast or flash release at high ironing or dryer temperature.

A further object of the invention is to provide a novel delivery system for olfactive compositions comprising different fragrant molecules with significantly improved sustained release of the entire olfactive composition and particularly of the most volatile top notes during and after application.

A further object of the present invention is to increase the olfactive performance of detergents, fabric softeners, body care and home care products and cosmetics with respect to perfuming of fabrics, solid surfaces, hair and skin.

The present invention relates to polymeric nanoparticles including olfactive components, having the above characteristics and a glass temperature of >50° C., obtainable by
  a) continuously adding a liquid monomer component and an olfactive component to an aqueous solution of a first initiator comprising an emulsifier and distributing the added components in the aqueous solution to obtain a reaction mixture while starting polymerisation of the monomer component in the reaction mixture at a first temperature and,
  while continuing the addition of the liquid monomer component and the olfactive component, adding a second initiator dropwise to the reaction mixture while maintaining the first temperature
  b) after terminating the addition of the liquid monomer component and the olfactive component increasing the temperature of the reaction mixture to a second temperature and dropwise adding a third initiator.

It has to be emphasised that the addition of the monomer component and the olfactive component has to be continued during the whole step a).

It is assumed that under this conditions the polymer particles of the invention are imprinted by the molecules of the olfactive composition, i.e. the polymer is formed around the individual olfactive components. Such polymers are also called template polymers. (Molecular) imprinting is characterised by (i) an enhanced retention of the olfactive components in the particles and (ii) a reduced diffusion of these olfactive components through the polymer. The overall retention/release profile of (molecularly) imprinted polymers is suitable to satisfy the objects of the present invention. Polymers obtained by batch radical polymerization, where the whole monomer component and olfactive component is present in the reaction mixture before polymerization starts, do not satisfy the objects of the present invention. Similarly, the process described above yields nanoparticles that perform better in their controlled release behaviour than perfumed nanoparticles obtained by absorbing an olfactive component into pre-formed nanoparticles. It has been surprisingly found that the olfactive components do generally not suffer from the polymerization conditions. It is also surprising that template polymers can be obtained with the generally small and highly volatile molecules of top notes.

Further it is also surprising that the formation of imprinted or template polymers according to the invention do not require the addition of large amounts of cross-linking agents in the reaction mixture.

In has to be emphasised that the addition of the monomer component and the olfactive component has to be continued dyring the whole step a).

It is assumed that under this conditions the polymer particles of the invention are imprinted by the molecules of the olfactive composition, i.e. the polymer is formed around the individual olfactive components. Such polymers are also called template polymers. (Molecular) imprinting is characterised by (i) an enhanced retention of the olfactive components in the particles and (ii) a reduced diffusion of these olfactive components through the polymer. The overall retention/release profile of (molecularly) imprinted polymers is suitable to satisfy the objects of the present invention. Polymers obtained by batch radical polymerization, where the whole monomer component and olfactive component is present in the reaction mixture before polymerization starts, do not satisfy the objects of the present invention. Similarly, the process described above yields nanoparticles that perform better in their controlled release behaviour than perfumed nanoparticles obtained by absorbing an olfactive component into pre-formed nanoparticles. It has been surprisingly found that the olfactive components do generally not suffer from the polymerization conditions. It is also surprising that template polymers can be obtained with the generally small and highly volatile molecules of top notes.

Further it is also surprising that the formation of imprinted or template polymers according to the invention do not require the addition of large amounts of cross-linking agents in the reaction mixture.

An additional advantage of the polymeric nanoparticle of the invention is the extremely low amount of monomers found. The amount of the principal monomer component is found in an amount of 100 ppm or less the principal monomer component being added during the process of the invention in a significantly higher amount than the other monomer(s).

The above process is also called semicontinous batch polymerization.

The polymerization takes place in a two phase system and homogenous distribution of the liquid monomer and the olfactive composition in the aqueous solution of the emulsifier is important. The two phase polymerization is either a dispersion, suspension or preferably an emulsion or mini-emulsion polymerization. For the latter a pre-emulsion is prepared by admixing the monomer with the olfactive composition and adding the pre-emulsion during step a) to the aqueous solution.

Optionally the aqueous solution may comprise dispersed polymer seeds.

Depending on the desired particle size, size distribution, fragrance release performance, etc., the steps of the above process can be modified. The rate of the addition and the droplet size of the olfactive and the monomer component and the initiator can be varied to obtain the desired particle properties. In particular, step a) can be followed by the addition of additional monomers and initiators, in order to provide an outer layer or coating of desired character on the particles. Also, the composition of the monomer and the olfactive component can be continuously varied in order to provide a gradient of characteristics within the particles. Such variations include: (i) variation of the temperatures, (ii) changing one or more initiators and/or initiator concentrations, (iii) changing feed rate of the monomer and olfactive component, (iv) changing the period of the above steps.

The composition of the monomer is particularly relevant to the particle performance. Monomer yielding polymers with a high glass transition temperature are particularly suitable. These encompass for example, styrene, methyl (meth)acrylate, isobornyl (meth)acrylate, adamantyl (meth) acrylate and (meth)acrylic acid, acrylamide and monomers of the general formula $=C(R^1)-CO-(CH_2)_n-X^+\ Y^-$, wherein $R^1$ is H or $CH_3$; n is 1 or 2, X is either a trimethyl quaternary ammonium or a dimethyl sulfonium radical and $Y^-$ is a counterion.

Preferred monomers are styrene, methyl(meth)acrylate and (meth)acrylic acids.

Cross linking monomers particularly useful for the present invention comprise divinyl benzene, trivinyl benzene, divinyl toluene, trivinyl toluene, di- and tri-acrylates like diesters—formed by (meth)acrylic acid and diols—and higher esters—formed by (meth)acrylic acid and polyols. Preferred are divinyl benzene, triethylenglycol dimethacrylate, tetraethylenglycol dimethacrylate, allylmethacrylate, diallylmaleate, triallylmaleate and 1,4-butanediol diacrylate.

The choice of emulsifier is less critical. Useful emulsifiers for emulsion and mini-emulsion polymerization can be anionic, cationic, zwitterionic or non-ionic. Examples of useful emulsifiers are given in Table 1:

TABLE 1

| Trade Name | Common Name | Remarks |
| --- | --- | --- |
| Rewoquat ® RTM50 | Ricinoylamidopropyltrimethyl-ammoniummetho sulfate | cationic |
| Rewoquat CPEM | Cocopentylethoxymethyl-anunoniummetho sulfate | cationic |
| Ethoquat ® C12 | Cocobis(2-hydroxyethyl) methylammonium chloride | cationic |

TABLE 1-continued

| Trade Name | Common Name | Remarks |
| --- | --- | --- |
| CTAB | Cetyltrimethylammonium bromide | cationic |
| Lexemul ® AR | Glyceryl stearate (and) Stearamidoethyl diethylamine | cationic |
| Disponil ® A1080 | Mixture of ethoxylated linear fatty alcohols | nonionic |
| Disponal ® A3065 | Mixture of ethoxylated linear fatty alcohols | nonionic |
| Mergital ® LM4L | Mixture of $C_{12}$–$C_{13}$ fatty alcohols ethoxylated with 4 moles of ethylene oxide | nonionic |
| Lauropal ® 12 | Mixture of $C_{12}$–$C_{14}$ fatty alcohols ethoxylated with 6–15 moles of ethylene oxide | nonionic |
| Montane ® 60 | Sorbitan stearate | nonionic |
| Tween ® 20 | Polysorbate 20 | nonionic |
| Tween ® 80 | Polysorbate 80 | nonionic |
| Triton ® X 165 | Stearate | nonionic |
| Tego Betain F 50 | Cocoamidopropylbetaine | zwitter-ionic |
| Betain Tego CK | Fatty acid alkyl amido alkylbetaine | zwitter-ionic |
| Dowfax ® 2A1 | Disulfonated surfactant with tetrapropylene hydrophobe source | anionic |
| SDS | Sodium dodecyl sulfate | anionic |
| Abex ® 3594 | | anionic |
| Abex ® EP-227 | Ammoniumnonoxynol-77 sulfate | anionic |
| Lexemul ® AS | Glyceryl stearate (and) Sodium lauryl sulfate | anionic |

Preferred are SDS, Abex ® 3594 and Dowfax ® 2A1 which are common emulsifiers for polystyrene particles.

Alternatively, polymer emulsifiers can be used, either as hydrocolloid stabilizing agents or as emulsifiers. Hydrocolloids of interest are poly(vinylalcohol-co-vinylacetate) copolymers, modified cellulose, polyoxyethylene and polyvinylpyrrolidon. Polymer surfactants are for example multiblock copolymers and graft copolymers containing at least one hydrophilic block and at least on hydrophobic block, like polyoxyethylene-polyoxypropylene-polyoxyethylene (PLURONIC) copolymers, polyether-modified dimethicones and polyether-alkyl-dimethicones (ABIL) copolymeres. Cationic silicones and polymers containing polyimide moieties may be also useful.

Initiators useful for emulsion polymerization are water-soluble initiators like peroxodisulfates, organic peroxides, hydroperoxides and water soluble azo-compounds. Specific examples of suitable initiators are ammonium persulfate, sodium persulfate, potassium persulfate, 1,4-diisopropyl-benzene hydroperoxide, cumene hydroperoxide, 2,2'-azobis (2-methylpropio-namidine)dihydrochlorid and 4,4'-azobis (4-cyanovaleric acid).

Preferred are the redox systems of ammonium- or sodium persulfates with iron (II) sulfate which allow thermic initiations at low temperatures.

Among the huge variety of fragrant materials used in perfumery, the following volatile compounds are particularly suitable as imprinting agents.

List of the olfactive components (OV: Odor value)

TABLE 2

| Chemical Abstracts Name | OV |
| --- | --- |
| ETHYL 2-METHYL PENTANOATE | 62586530 |
| ETHYL ISO BUTYRATE FCC | 39200330 |

TABLE 2-continued

| Chemical Abstracts Name | OV |
|---|---|
| BUT-2-ENE-1-ONE,1-(2,6,6-TRIMETHYL-1,3-CYCLOHEXADIEN-1-YL)- | 21672290 |
| NONADIENAL 1% CITROFLEX | 17446920 |
| PHENYL ACETALDEHYDE 85 | 14342060 |
| INDOLE, 3-METHYL | 10531770 |
| HEXANOIC ACID, ETHYL ESTER | 10296830 |
| 1,8-EPOXY-PARA-METHANE | 9931397 |
| ALDEHYDE C12 MNA | 9648383 |
| ETHYL ACETATE | 7672145 |
| ETHYL-2-METHYL BUTYRATE | 6716841 |
| ALDEHYDE C8 | 5678510 |
| TRANS DECEN-4-AL | 4668142 |
| UNDECATRIENE | 4482573 |
| METHYL OCTYL ACETALDEHYDE | 4469274 |
| ALDEHYDE C7 | 3699238 |
| 2,6 DIMETHYL-5-HEPTENAL | 3674714 |
| DIHYDRO 2-METHOXY-4-(2-PROPENYL) PHENOL | 3472000 |
| BUTYL PHTHALIDE | 3266946 |
| LIME OXIDE | 2161723 |
| ETHYL BUTYRATE | 1764598 |
| NONENOL, CIS-6 | 1712805 |
| PARA-TOLYL ALDEHYDE EXTRA | 1475808 |
| DIHYDRO ANETHOLE FCC | 1313749 |
| CYCLO HEXYL ACETATE | 1292485 |
| PARA-CRESYL ACETATE | 1273204 |
| PYRAN,2,4-DIMETHYL-6-PHENYL-DIHYDRO-3-(3-ISOPROPYLPHENYL)BUTANAL | 1193400 |
| | 1187323 |
| BUT-2-ENE-1-ONE,1-(2,6,6,-TRIMETHYLCYCLOHEX-1-EN-1-YL)- | 1122995 |
| METHYL 2-OCTYNOATE | 1094551 |
| BUTYL ACETATE, ISO, FCC | 979809.6 |
| 7-METHYL-3,4-DIHYDRO-2H-1,5-BENZODIOXEPIN-3-ONE | 973365.4 |
| 2-BUTEN-1-ONE,1-(2,6,6-TRIMETHYL-1,3-CYCLOHEXEN-1-YL)- | 961551.6 |
| 2-METHOXY-4-METHYLPHENOL | 943751.4 |
| 4-METHOXYBENZALDEHYDE | 941980.3 |
| OCTENOL | 925978.5 |
| BICYCLO[3.1.1]HEPT-2-ENE-2-PROPANAL,6,6-DIMETHYL | 904490.6 |
| ACETIC ACID, 3-METHYL-2-PROPENYL ESTER | 877798.3 |
| ALDEHYDE ISO C11 | 854722 |
| 3,7-DIMETHYL-2,6-OCTADIENENITRILE | 832569 |
| METHYL ANTHRANILATE | 827264.3 |
| METHYL OCTALACTONE | 826643 |
| METHYL PHENYL ACETATE | 792198.8 |
| METHYL IONONE/IRISANTHEME | 778605.1 |
| DIMETHYL ACETOPHENONE,2,4 | 754754.7 |
| 8-ETHYL-1-OXASPIRO[4.5]DECAN-2-ONE | 734286 |
| 4-METHOXYBENZALDEHYDE | 683617.5 |
| CYCLOHEX-2-EN-1-ONE,2-METHYL-5-(1-METHYLETHENYL) | 673272.8 |
| PHENYL PROPYL ALDEHYDE | 589314.7 |
| ALLYL AMYL GLYCOLATE | 587664.6 |
| 2,4 DIMETHYL 3 CYCLOHEXEN-1-CARBALDEHYDE | 587309.8 |
| CYCLOHEX-3-ENE,1-CARBOXALDEHYDE,2,4-DIMETHYL- | 585468 |
| HEXENYL ACETATE, CIS-3- | 575465.8 |
| 7-METHYL-3-METHYLENE-1,6-OCTADIENE | 546499.8 |
| PARA CRESOL | 524810.3 |
| ISO NONYL ALDEHYDE | 510654.2 |
| ALDEHYDE C18 | 507873.9 |
| CYCLOPENT-2-EN-1-ONE, 2-HEXYL- | 485812.6 |
| ISO PROPYL QUINOLINE/BASE 3 | 479565.3 |
| 2-PHENLYPROPANAL | 477838.4 |
| AMYL ACETATE | 441261.3 |
| BUTYL ACETATE | 435143.8 |
| METHYL LAITONE | 420065.1 |
| ALDEHYDE C14 | 419891.6 |
| HEXENOL, CIS-3- | 391510 |
| ALDEHYDE C10 | 387743.2 |
| BUTYRIC ACID, 2-METHYL-,HEXYL ESTER | 382190.6 |
| ETHYL PHENYL ACETATE | 375894.8 |
| ACETIC ACID, (CYCLOHEXYLOXY)-, 2-PROPENYL ESTER | 372893.1 |

TABLE 2-continued

| Chemical Abstracts Name | OV |
|---|---|
| DEC-4-EN-1-AL | 367957 |
| METHYL HEXYL KETONE | 361139.4 |
| FORMYL-7-ISOPROPYL-5-METHYL-2-BICYCLO[2.2.2.]OCT-2-ENE | 355730.8 |
| 2,6 DIMETHYLHEPTAN-2-OL | 352155.6 |
| ALDEHYDE C11 UNDECYLENIC | 351095 |
| TRANS 2 HEXENAL | 350064.3 |
| 2-METHOXY-4-(2-PROPENYL)PHENOL | 346904.9 |
| 3.7-DIMETHYLOCTANAL | 311427.9 |
| ETHYL HEPTOATE | 310684.7 |
| 3,7-DIMETHYL-2,6-OCTADIENENITRILE | 298260.5 |
| CYCLOHEX-1-ENE 4-CARBOXALDEHYDE-1,3,5-TRIMETHYL | 295165.8 |
| PYRAN, TETRAHYDRO-4-METHYL-2-(2-METHYL-1-PROPENYL)-2H | 291002 |
| METHYL PHENYL ETHYL OXYDE | 287117.9 |
| HEXENYL FORMATE, CIS-3- | 282721.5 |
| BUT-3-EN-2-ONE, 4-82,6,6-TRIMETHYLCYCLOHEX-1-EN-1-YL) | 280385 |
| HEX-5-EN-2-ONE | 278762.7 |
| CARYOPHYLLENE FCC ,NATURAL NKFP | 278378 |
| PARA METHYL ACETOPHENONE | 271792.6 |
| JASVERATE | 265515.9 |
| NONA-6,8-DIEN-3-ONE, 2,4,4,7-TETRAMETHYL | 252222 |
| DIHYDRO 3,7 DIMETHYL-1,6-OCTADIEN-3-OL | 250072.3 |
| OCT-7-EN-2-OL, 2,6-DIMETHYL | 248873.6 |
| 2-BUTEN-1-ONE,1-(2,6,6-TRIMETHYL-2-CYCLOHEXEN-1-YL)- | 245891.4 |
| BUT-2-ENE-1-ONE,1-(2,6,6-TRIMETHYL-3-CYCLOHEXEN-1-YL) - | 243343.3 |
| METHYL AMYL KETONE | 239523.8 |
| CYCLOHEXENE, 1-METHYL-4-(1-METHYLETHYLIDENE) | 234817.8 |
| CITRODYLE | 230257.8 |
| ALPHA ISO METHYLIONONE | 218736.2 |
| 3,7 DIMETHYL-1,6-OCTADIEN-3-OL | 218426.5 |
| METHYL OCTINE CARBONATE | 216945.5 |
| ACETOPHENONE EXTRA | 212908.8 |
| 4-PENTEN-2-OL, 3-METHYL-5-(2,2,3-TRIMETHYL-3-CYCLOPENTEN-1-YL) | 212557.4 |
| OCTALACTONE, GAMMA | 210058.7 |
| INDOLE PURE | 207042.8 |

The fragrances are present in an amount of 5 to 50%, preferably 10 to 30% with respect to the dry polymer, and 1.4 to 14%, preferably 3.5 to 10.5% with respect to a polymer dispersion.

A typical nanoparticle of the invention comprises:
  67% by weight of a copolymer phase consisting e.g. of 92% by weight of styrene, 2% by weight of divinyl benzene and 6% by weight of methacrylic acid,
  ca. 30% by weight olfactive components,
  0.6 to 3% by weight of the total composition of an emulsifier as stabiliser e.g. comprising SDS, Abex® 3594, Dowfax®, 2A1, Lexemul® AS and Mergital® LM4L.

The nanoparticles may be supplied or used suspended in water as latex or in solid dried form. The latex form does preferably contain not more than 70% by weight of the nanoparticles of the invention.

The effect of long lasting release of olfactive component is particularly pronounced when the latex is added to a conditioning composition. Significantly improved deposition, sustained release at room temperature and fast release at higher temperature are also found when the latex is added to rinsing water without softening components.

The design of a latex for use in fabric care and hair conditioners constitutes a preferred embodiment of the present invention. Fabric care and hair conditioners comprise typically of cationic surfactants having a high affinity to fabrics and hair and providing desired softening action and esthetic shine.

The prior art teaches how to formulate perfumed particles in consumer products like liquid detergents and conditioners. A classical strategy involves the addition of particles bearing the same electrical charge as the principal surface active agent present in the product composition. Hence, particles disclosed so far for use in fabric care or hair conditioners are positively charged in order to increase their compatibility with the cationic actives present in the product. Similarly, negatively charged particles are thought to be compatible with the anionic cleansing active present in liquid detergents. It has now been surprisingly found that the above restrictions do not apply to the nanoparticles of the present invention. By choosing suitable functional monomers and emulsifiers, nanoparticles bearing an opposite charge with respect to the principal surfactant of the end product, excellent controlled release properties can be gained, without affecting the stability of the end product. Hence, surprisingly, anionic, hard, glassy, nanoparticles of the invention when added to a cationic liquid conditioner are specially suitable for imparting long lasting delivery of top notes on fabrics and hair over a long period of time and fast release of the olfactive component upon heating. Nanoparticles that are particularly suitable for use in fabric care and hair care conditioners are produced by polymerizing a mix containing 5 to 50%, preferably 10 to 30% of olfactive components, 40 to 95% styrene, 0 to 10% divinyl benzene, 0 to 10% (meth)acrylic acid and 0.5 to 3% anionic emulsifier by emulsion polymerization. The nanoparticles with sizes in the range of several hundred nanometers can be mixed directly with the fabric conditioner and deposited onto the fabrics. Soak test an olfactory evaluation confirms a sustained release of olfactive components during the drying stage and the storage.

Therefore, the strategy disclosed in the preferred embodiments of the present invention involves the use of negatively charged nanoparticles in consumer products containing cationic surfactants as principal surface active agents and positively charged nanoparticles in consumer products containing anionic surfactants as principal surface active agents. As shown in the examples below this strategy leads to products with excellent performance.

The surface potential of the nanoparticles is believed to control the stability of the nanoparticles in the end product. The surface potential of a colloid particle depends on a number of factors like (i) the amount of ionized chemical groups present on the surface, (ii) the nature of the emulsifier adsorbed on the particle and (iii) the amount of counterions present in the vicinity of the nanoparticle. If the partially ionizable groups consist of weak acids or weak bases, the surface potential will be also controlled by the pH of the dispersion medium. The surface potential of colloid particles is usually measured by measuring the so-called zeta-potential of the particles. A complete definition of zeta-potential can be found for example in (R. J. Hunter. "Zeta Potential in Colloid Science", Academic Press, London, 1981). The zeta-potenial of particles in a diluted dispersion can be measured by electroosmosis and electrophoresis, whereas in concentrated dispersions, electrokinetic sonic amplitude measurements are preferred. It has been shown for optimal stability in end products containing electrically charged species, the zeta-potential should not exceed some critical values, which depend on the nature and composition of the end products. For typical fabric care and hair care conditioners containing up to 5% cationic surfactants and a pH of 2.5, the critical value of the zeta-potential is estimated to −35 mV. For typical liquid detergents or cleansing compositions containing up to 10% anionic surfactants and a pH of 8, this critical values will lie around +18 mV.

Significant enhancement of deposition means, a measurable increase of the fragrance concentration on the substrate measured by solvent or thermal extraction.

Significantly improved sustained release of the olfactive components means a perceivable fragrance concentration in the headspace surrounding the dry fabric after 5 days. The sustained release is checked after 24 hours, during 5 days by olfactive evaluation by at least 5 pannelists.

Significantly improved fast release at higher temperature of the olfactive components means an unambiguous increase of the concentration in the headspace surrounding the dry fabric during and after thermic treatment, as measured by thermic extraction and olfactive evaluation by at least 5 panelists.

The delivery system of the invention can be used in detergents or fabric conditioners, rinsing compositions for fabrics, body cleansing composition, hard surface cleaners, rinse off hair conditioners, cosmetic compositions or spray applications, e.g. on carpet and furniture. These compositions may be prepared by adding the delivery system to an unperfumed detergent or fabric conditioning composition, or to water as a rinsing composition for fabrics, or to rinse off hair conditioning or cosmetic composition. Further, the compositions of the invention may be perfume dispensers in form of a solid composition or applied to a solid carrier, or air fresheners.

The following examples show a preferred embodiment of the invention without limiting it.

EXAMPLE 1

Preparation of a Latex Containing Nanoparticles

A pre-emulsion is prepared by mixing an aqueous phase, prepared by dispersing the surfactants Abex® 3594 (8 g) and SDS (4 g) in water (100 g), with an organic phase containing styrene (276 g), methacrylic acid (18 g), divinylbenzene (6 g) and the olfactive component (40 g) (see Table 2, below). The aqueous and the organic phase are mixed, vortexed, homogenised (Ultraturrax® homogeniser) and flushed with nitrogen. The pre-emulsion has to be stable for more than 24 hours.

A 1 l reaction flask equipped with a stirrer, reflux condenser, thermometer and inlet tube for delivery from a peristaltic pump is placed in a water bath at 75° C. During nitrogen rinsing, a first initiator $I_1$ (6 g $Na_2S_2O_8$/30 ml water) is added dropwise into the reaction flask which contains 100 ml water, 0.3 g buffer ($NaHCO_3$), 0.5 g Abex® 3594 and a small amount of iron(II) sulfate. After 30 minutes the pre-emulsion and a second initiator $I_2$ (3 g $Na_2S_2O_8$/60 ml water) are separately added dropwise into the reaction flask under stirring at 420 rpm, using peristaltic pumps over a period of about 120 minutes. After terminating the addition, the reaction mixture is stirred for further 30 minutes and the bath temperature is increased up to 88° C. Subsequently a third initiator $I_3$ (0.7 g $Na_2S_2O_8$/30 ml water) is added dropwise over a period of 30 minutes before the reaction mixture is cooled to room temperature. Finally the latex particles are filtered through a 150 micrometer sieve.

The olfactory performance of each sample is evaluated by a panel of at least 5 trained evaluators against that of a reference sample.

EXAMPLE A

Variation of the Methacrylic Acid Amount
0%, 2.6%, 5.2%, 7.8% of the polymer dispersion.

TABLE 3

Olfactive performance for example A and general stability of the polymer dispersion

| Methacrylic acid amount [%] | Olfactive Performance | | | Stability* of the polymer dispersion |
|---|---|---|---|---|
| | 24 h | 48 h | >72 h | |
| 0 | + + | + | + | − |
| 2.6 | + + + | + + | + | + |
| 5.2 | + + + | + + | + + | + |
| 7.8 | + + | + + | + + | + |

*Stability of the polymer dispersion:
agglomeration after 1 week: −
no agglomeration after 1 week: +

EXAMPLE B

Variation of the Amount of Perfume A and B
5.9%, 11.7% of the polymer dispersion after five days.

TABLE 4

Olfactive performance for example B

| perfume amount [%] | Olfactive Performance | |
|---|---|---|
| | perfume A | perfume B |
| 5.9 | + + | + + |
| 11.7 | + + | + + |

EXAMPLE C

Variation of the Amount of Perfume C
2.9%, 5.9%, 11.7%, 17.7% of the polymer dispersion.

TABLE 5

Olfactive performance for example C after 5 days

| perfume amount [%] | Olfactive Performance | Latex stability |
|---|---|---|
| 2.9 | + | + |
| 5.9 | + + | + |
| 11.7 | + + | + |
| 17.7 | + | + |
| 35 | + | stability limit |

EXAMPLE 2

Preparation of a Transparent Latex Containing Nanoparticles

A 100 ml reaction flask equipped with a stainless steel stirrer, reflux condenser, thermometer and a nitrogen inlet is placed into a oil bath at 88° C. 0.6 g SDS is solved in 37 g water and charged into the reaction flask. 9 g Styrene is mixed with 1 g of the olfactory component, charged into the reaction flask with stirring and purged with nitrogen gas. After 30 min the temperature is equilibrated (80° C.) and the reaction is started by injection an appropriate amount of aqueous 2,2'-azo-di(poly(ethylene glycol) isobutyrate solution (0.673 g PEG 200-initiator/3 ml $H_2O$). After 3 hours stirring at 80° C. the polymerization is completed and the reaction mixture is cooled to room temperature. Finally, the latex particles are filtered through a 20 micrometer filter.

EXAMPLE 3

Preparation of a Latex Containg Core-Shell Nanoparticles

A pre-emulsion is prepared by mixing an aqueous phase prepared by dispersing the surfactant SDS (0.2 g) in water (95 g), with an organic phase containing styrene (40 g) and the olfactory component (6 g). The aqueous phase and the organic phase are mixed, vortexed, homogenised (Ultraturrax® homogeniser) and flushed with nitrogen. The pre-emulsion has to be stable for more than 24 hours.

A 300 ml reaction flask equipped with a stirrer, reflux condenser, thermometer and inlet tube for delivery from a peristaltic pump is placed in a oil bath at 61° C. During nitrogen rinsing, a first initiator $I_1$ (3.5 ml $Na_2S_2O_8$ 1 mol/L) is added into the reaction flask which contains 30 ml water, 0.1 g buffer ($NaHCO_3$), 0.08 g SDS and a small amount of iron (II) sulfate. After 30 minutes the pre-emulsion and a second initiator $I_2$ (2 ml $Na_2S_2O_8$ 1 mol/L) are separately added dropwise into the reaction flask under stirring, using peristaltic pumps over a period of about 120 minutes. After terminating the addition, the reaction mixture is stirred for further 150 minutes. Subsequently the methyl methacrylate shell is formed by adding a mixture of methyl methacrylate (20 g), methacrylic acid (0.5 g), ethylene glycol dimethacrylate (0.15 g) and the olfactory component (0.08 g) dropwise over a period of 75 minutes into the reaction flask. Simultaneously, initiator $I_3$ (2 ml $Na_2S_2O_8$ 0.2 mol/L) is added dropwise and the reaction mixture is stirred for further 75 minutes before it is cooled to room temperature. Finally the latex particles are filtered through a 150 micrometer sieve.

EXAMPLE 4

Hair or Fabric Conditioner 7 g of the conditioner base is mixed with various amounts of a latex comprising nanoparticles obtained according to Example 1. The amounts of polymer dispersion are chosen in such a way that 1% with reference to the amount of conditioner of perfume composition is included. The mixture is intensively vortexed and homogenised by an Ultraturrax® homogeniser.

EXAMPLE 5

Assessment of Storage Stability

The stability of different mixtures of softener and polymer dispersion are investigated over a period of one month. Depending on the composition of the polymer dispersion, i.e. the amount of methacrylic acid, amount of fragrance, pH-value and temperature, some mixtures are becoming gel-like. The following table shows the stability for the latex of Example 1 in a dispersion of Example 2.

TABLE 6

| Amount of softener | Amount of dispersion | 1 day | 4 days | 10 days | 1 month |
|---|---|---|---|---|---|
| 7 g | 1.200 g | Gel | Gel | Gel | Gel |
| 7 g | 1.008 g | Liquid | Gel | Gel | Gel |
| 7 g | 0.806 g | Liquid | Liquid | Liquid | Liquid |
| 7 g | 0.495 g | Liquid | Liquid | Liquid | Liquid |
| 7 g | 0.310 g | Liquid | Liquid | Liquid | Liquid |

EXAMPLE 6

Rinse Test 1.6 g of the fabric conditioner/latex mixture according to Example 4 is diluted in 1 l of cold water. A dry cotton towel of 50 g is given into the mixture and washed at room temperature by rotating intensively for 10 minutes. Finally the towels are spin dried for 1 minutes and installed on a line dryer for 5 days. The olfactory performance of each sample is evaluated by a panel of at least 5 trained evaluators against that of a reference sample without nanoparticles as a function of time.

The result of the panel test release of perfume A from dry fabrics as a function of time is shown in FIG. 1.

EXAMPLE 7

Headspace Analysis

The concentration of fragrances in the headspace surrounding towels handled, as in Example 6, with a fabric care conditioner with fragrance added (Reference) and with nanoparticles of the invention A added. 50 ml headspace were pumped through a Porapak® adsorber cartridge for one minute. The adsorbed fragrances are then extracted with 50 microliters hexane and the whole extract is injected into a large volume injection port of a gas chromatograph equipped with a capillary column. The area counts (arbitrary units) of each test substances are reported on Table 7.

TABLE 7

| Perfume Component | $t_R$ | Area counts after 24 h Reference | Area counts after 24 h Sample |
|---|---|---|---|
| Amylacetat | 8.82 | 0 | 730 |
| Eucalyptol | 9.60 | 27 | 6664 |
| Dimethyloctenon | 12.52 | 20 | 4086 |
| Cyclal C | 13.54 | 0 | 3266 |
| Linalol | 16.99 | 0 | 14 |
| Aldehyde C12 | 19.33 | 67 | 984 |
| Viridine | 21.15 | 0 | 0 |
| Terpineol | 21.60 | 0 | 253 |
| Benzylacetat | 22.64 | 0 | 21 |
| Alpha-ionone | 26.52 | 0 | 238 |
| Compound X | 27.54 | 0 | 237 |
| Phenyl ethyl alcohol | 28.77 | 9 | 13 |
| Diphenyloxide | 31.66 | 30 | 747 |
| Compound Y | 32.28 | 11 | 130 |
| Lilial | 33.00 | 116 | 131 |

The results show clearly the remanence of the volatile top notes in the headspace of the towel after 24 hours drying.

EXAMPLE 8

Determination of Unreacted Monomer 3 g of polymerdispersion according to example 1 is weighted into a 10 ml head space vial and analyzed by a SPME (solid phase micro extraction) head space analysis at 35° C., and compared to a sample doped with pure monomers.

According to example 1 a styrene content of 50 ppm is found.

The invention claimed is:

1. Polymeric nanoparticles including olfactive components and having a glass temperature of >50° C. obtained by
   (a) continuously adding a liquid monomer component and an olfactive component to an aqueous solution of a first initiator comprising an emulsifier and distributing the added components in the aqueous solution to obtain a reaction mixture while starting polymerization of the monomer component in the reaction mixture at a first temperature and,
   while continuing the addition of the liquid monomer component and the olfactive component, adding a second initiator dropwise to the reaction mixture while maintaining the first temperature;
   (b) after terminating the addition of the liquid monomer component and the olfactive component increasing the temperature of the reaction mixture to a second temperature and dropwise adding a third initiator.

2. Nanoparticles according to claim 1 having a particle size of <3–10$^{-6}$ m.

3. Nanoparticles according to claim 1 comprising 5 to 50%, by weight of olfactive components.

4. Nanoparticles according to claim 3 wherein the olfactive component has an odor value between 10,000 and 10,000,000.

5. Nanoparticles according to claim 1 comprising a body part and an outer layer or coating part whereby the two parts are formed by different polymers.

6. Nanoperticles according to claim 1 having characteristics changing from center to the surface of the particles.

7. Nanoparticles according to claim 1 selected from polystyrene and acrylic polymers.

8. Nanoparticles according to claim 1 comprising a crosslinked polymer.

9. Nanoparticles according to claim 1 comprising a template polymer including the olfactive components.

10. Nanoparticles according to claim 1 whereby up to 70% by weight of nanoparticles are suspended in a water phase as latex.

11. Nanoparticles according to claim 1 comprising residual monomer of 100 ppm or less of the principal monomer compound.

12. Nanoparticles according to claim 11 comprising 50 ppm or less of unreacted styrene of a styrene/acrylic acid polymer whereby styrene is the principal monomer component.

13. A method of preparing nanoparticles including olfactive components and having a glass temperature of <50° C. by
   (a) continuously adding a liquid monomer component and an olfactive component to an aqueous solution of a first initiator comprising an emulsifier and distributing the added components in the aqueous solution to obtain a reaction mixture while starting polymerization of the monomer component in the reaction mixture in the presence at a first temperature and, while continuing the addition of the liquid monomer component and the olfactive component, adding a second initiator dropwise to the reaction mixture while maintaining the first temperature;

(b) after terminating the addition of the liquid monomer component and the olfactive component increasing the temperature of the reaction mixture to a second temperature and dropwise adding a third initiator.

14. A method according to claim 13 whereby the olfactive component is a mixture of olfactive components and the composition of the mixture is varied during the addition thereof.

15. A method according to claim 13 whereby the temperature is varied during addition of the components.

* * * * *

UNITED STATES PATENT AND TRADEMARK OFFICE
CERTIFICATE OF CORRECTION

PATENT NO.         : 7,205,340 B2
APPLICATION NO.    : 10/240978
DATED              : April 17, 2007
INVENTOR(S)        : Quellet et al.

It is certified that error appears in the above-identified patent and that said Letters Patent is hereby corrected as shown below:

Column 14, line 59 claim 13, "of <50°C." should read -- of >50°C. --

Signed and Sealed this

Twenty-fourth Day of February, 2009

JOHN DOLL
*Acting Director of the United States Patent and Trademark Office*